United States Patent

Carchidi et al.

Patent Number: 5,899,940
Date of Patent: May 4, 1999

[54] MAXILLOFACIAL ANCHORING SYSTEM FOR ALVEOLAR AND SMALL BONE SKELETAL DISTRACTION

[76] Inventors: Joseph Edward Carchidi, 132 Samuel Ave., W. Bridgewater, Mass. 02379; Alan R. Balfour, 5452 Quailridge Dr., Camarillo, Calif. 93012

[21] Appl. No.: 09/013,433

[22] Filed: Jan. 26, 1998

Related U.S. Application Data

[60] Provisional application No. 60/037,903, Feb. 11, 1997.

[51] Int. Cl.[6] .................... A61F 2/28; A61F 2/02
[52] U.S. Cl. .................... 623/16; 623/16; 623/11
[58] Field of Search ............ 623/16, 11; 433/174; 606/73

[56] References Cited

U.S. PATENT DOCUMENTS

| | | | |
|---|---|---|---|
| 4,936,851 | 6/1990 | Fox et al. | 623/16 |
| 5,004,421 | 4/1991 | Lazarof | 433/173 |
| 5,527,183 | 6/1996 | O's Brien | 433/174 |
| 5,549,677 | 8/1996 | Durr et al. | 623/16 |
| 5,782,918 | 7/1998 | Klardie | 623/16 |

*Primary Examiner*—Mickey Yu
*Assistant Examiner*—Alvin Stewart
*Attorney, Agent, or Firm*—John A. Haug

[57] ABSTRACT

A maxillofacial anchoring and distracting system (10) is shown for lengthening the alveolar and small craniofacial skeletal bones by distraction osteogenesis. The distraction system includes a base plug (12), an internally and externally threaded anchoring screw body (14), a distraction jack screw (16) and healing screw (18). The base plug is press-fit into an osteotomy and acts as a baseplate to resist and transfer force received from the distraction jack screw to the subperiosteal corticotomy callus. The application of distraction force to the subperiosteal corticotomy via the distraction jack screw is resisted coronally by the anchoring screw body. Once the desired monofocal distraction osteogenesis has been completed, the maxillofacial anchoring and distraction system can be removed and easily replaced with an optimal length endosseous dental implant.

7 Claims, 3 Drawing Sheets

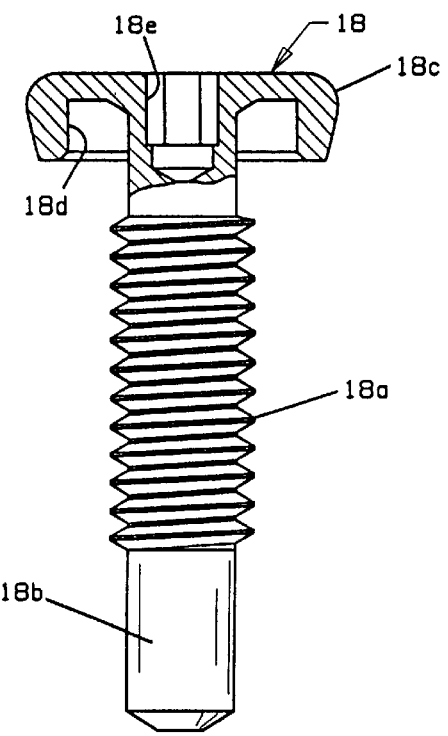
FIG 2
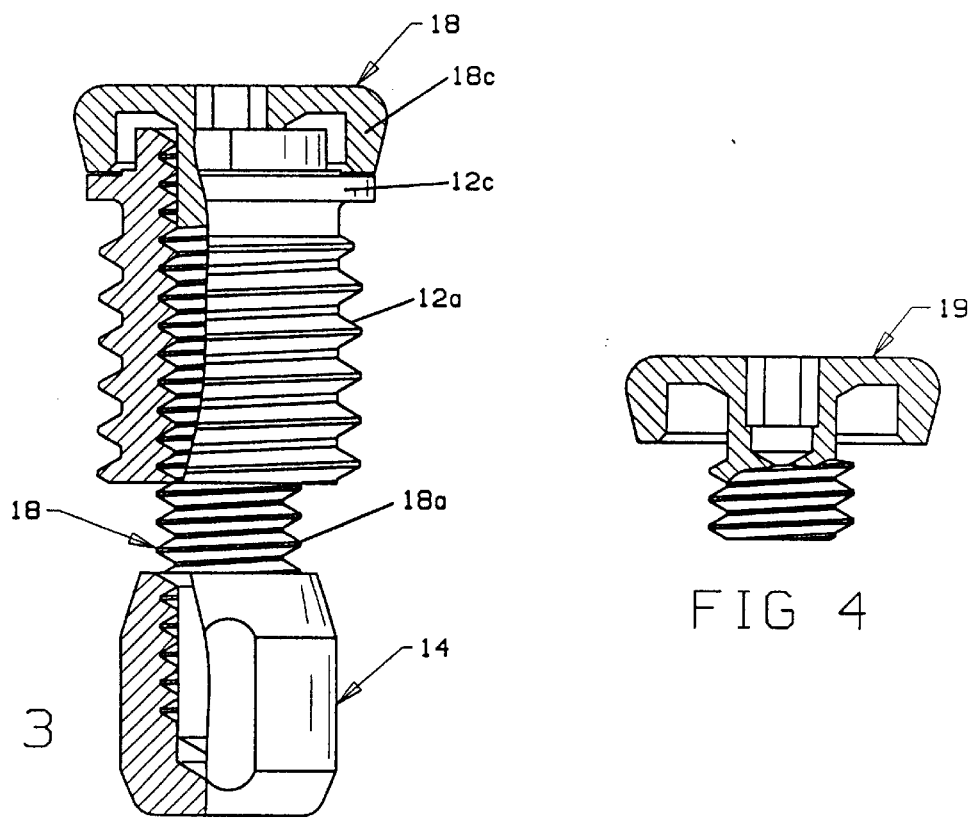
FIG 3
FIG 4

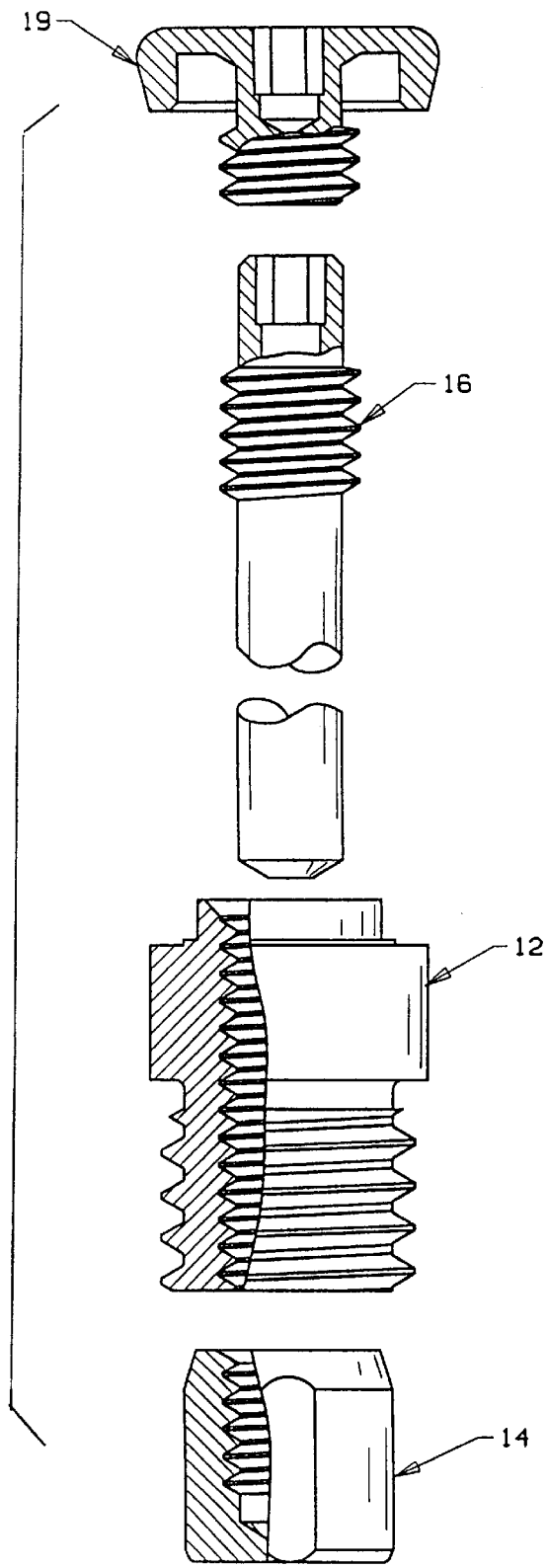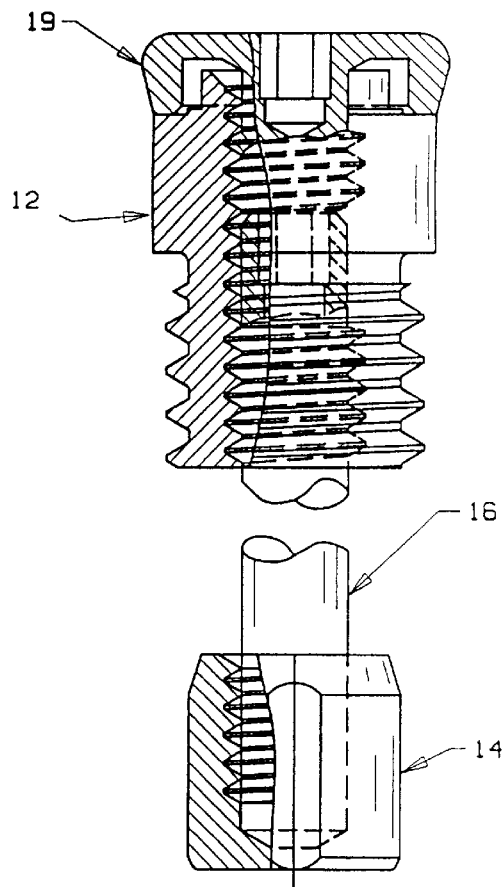
FIG 4a
FIG 4b

MAXILLOFACIAL ANCHORING SYSTEM FOR ALVEOLAR AND SMALL BONE SKELETAL DISTRACTION

This application claims priority from Provisional Application No. 60/037,903 filed Feb. 11, 1997.

FIELD OF THE INVENTION

This invention relates generally to anchoring and fixation systems for bone lengthening by monofocal distraction osteogenesis and more particularly to maxillofacial alveolar and small craniofacial skeletal bone distraction.

BACKGROUND OF THE INVENTION

The present invention addresses problems associated with regenerating maxillofacial bone mass to treat congenital or functional masticatory deficiencies. Conventionally, in order to restore masticatory deficiencies a patient with marginal bone mass is first treated with a surgical bone graft. Bone grafting techniques range from a harvested autogenous onlay graft to a synthetic hydroxyapatite bone mixture used to pack and build up the surgical site. Once the graft has healed, a second surgery is performed to insert the appropriate length endosseous dental implant and to restore masticatory function.

The process of bone grafting to regenerate bone mass has suffered from limited results. In many cases, at the time for surgical insertion of the endosseous dental implant, the grafting mass has significantly or completely resorbed away. One reason for the loss of this grafting material is the body's requirement for an applied stress to stimulate and maintain the bone mass. Furthermore, as documented cases have shown, if a synthetic filler is mixed with the harvested graft material, it is not uncommon for the filler material to migrate from the surgical site. This migration and degradation of the graft material minimizes the benefit of the procedure. These undesired results combined with the morbidity of the harvested area demonstrate the need for an alternative surgical procedure. In addition, these conventional multiple surgical procedures require a greater investment of time, money and available grafting materials than is desirable.

SUMMARY OF THE INVENTION

It is an object of the present invention to provide a system which overcomes the prior art limitations noted above. Another object is the provision of a procedure and apparatus for increasing bone mass of the alveolar and small craniofacial skeletal bones by monofocal distraction osteogenesis. Another object of the invention is to provide a system to perform monofocal distraction on a subperiosteal corticotomy. Yet another object of the invention is to provide a mechanical distraction unit that can be easily removed and replaced with endosseous dental implants.

Briefly described, in accordance with the invention, a maxillofacial anchoring and distracting system for bone lengthening osteogenesis comprises an internally threaded base plug that acts as a baseplate for resisting and translating the distraction force, an internally and externally threaded anchoring screw body for locking into the coronal portion of the corticotomy and a defined length distraction jack screw for applying the distraction force.

Upon preparation of an osteotomy the base plug and anchoring screw body are placed therein and the distraction jack screw is inserted. The distraction screw is advanced a selected amount on a periodic basis applying a distraction force on the base plug. When the desired amount of distraction has been achieved the jack screw is removed and replaced with a healing screw. After a suitable healing period the healing screw is removed followed by the anchoring screw body and the base plug. A suitable endosseous dental implant is then inserted in a conventional manner.

Additional objects and features of the invention will be set forth in part in the description which follows and in part will be obvious from the description. The objects and advantages of the invention may be realized and attained by means of the instrumentations, combinations and methods particularly pointed out in the appended claims.

BRIEF DESCRIPTION OF THE DRAWINGS

The accompanying drawings, which are incorporated in and constitute a part of the specification, illustrate a preferred embodiment of the invention and, together with the description, serve to explain the objects, advantages and principles of the invention. In the drawings:

FIG. 2 is a front elevational view, partly in cross-section, of a first stage healing screw for use with the anchoring screw body and base plug of FIG. 1;

FIG. 3 is a front elevational view, partly in cross-section, of the FIG. 2 healing screw received in the anchoring screw body and base plug of FIG. 1 as it would appear in a surgical site; and FIG. 4 is a front elevational view of a final healing screw, FIG. 4a is a view similar to FIG. 1 shown with the FIG. 4 healing screw and FIG. 4b is a view similar to FIG. 3 showing the FIG. 4a components as they would appear in a surgical site.

DETAILED DESCRIPTION OF PREFERRED EMBODIMENTS

Figure 1:
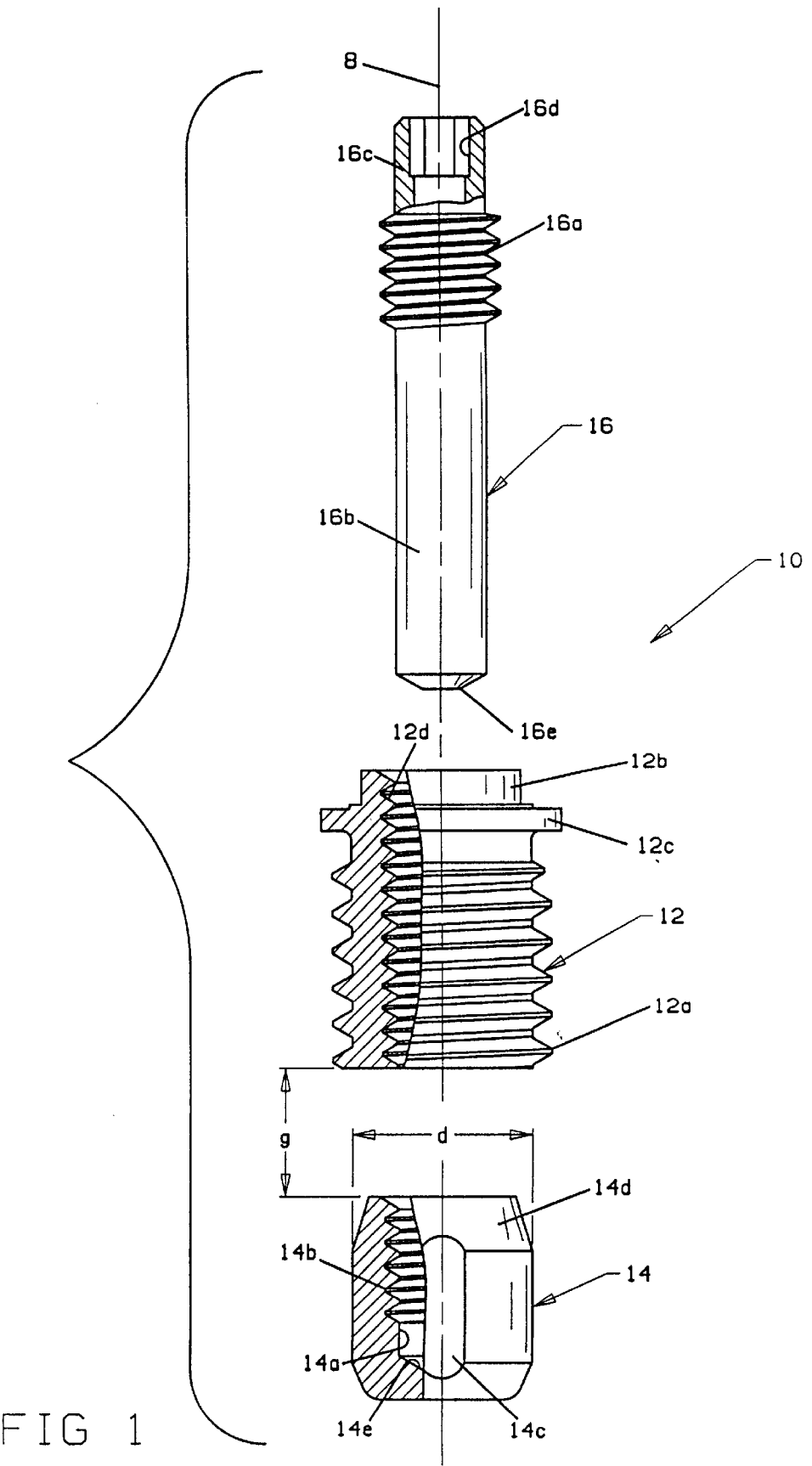
FIG. 1 is an exploded front elevational view, in enlarged scale, partly in cross-section, of the primary components of the maxillofacial anchoring and distracting system made in accordance with the invention.

With regard to FIG. 1, the maxillofacial anchoring and distracting system made in accordance with the invention is indicated by numeral 10 and comprises an anchoring screw body 12, an internally threaded base plug 14 and a defined length distraction jack screw 16.

Base plug 14 has a selected outer diameter d to provide a press-fit into the apex of a pre-drilled osteotomy having a longitudinal axis 8. Once inserted into the osteotomy, base plug 14 serves as a baseplate for resisting and translating the inward (in relation to the entrance to the osteotomy) distraction force from the distraction jack screw 16 to the subperiosteal corticotomy callus. To achieve this, base plug 14 includes a closed ended bore 14a having a threaded portion 14b adapted to receive the distal end of distraction screw 16 to be discussed below. Preferably, a pair of longitudinally extending flats or grooves 14c are formed in the outer surface of base plug 14 to eliminate any hydrostatic fluid pressure buildup and facilitate complete seating of the plug into the osteotomy. An elongated delivery and removal tool (not shown) having a threaded end portion can be used to engage threads 14b to assist in the seating procedure. Finally, when the desired monofocal distraction osteogenesis has been completed, base plug 14 can be extracted from the osteotomy by again engaging threads 14b of base plug 14 with the delivery and removal tool and pulling in an outward direction. Preferably, the coronal portion 14d of base plug 14 is tapered with the outer diameter of the tapered portion increasing in a direction going from the coronal end to the distal end of the base plug 14 for assisting in the removal process. The outer surface of base plug 14 is preferably provided with a smooth, polished outer surface to inhibit osseointegration and further assist in the removal process.

Once the appropriate internally threaded base plug 14 is inserted and rigidly seated at the bottom of the osteotomy, an anchoring screw body 12 with a selected external thread 12a, length and diameter, is screwed in cutting a thread into the bone and filling the upper region of the surgical site. Anchoring screw body 12 preferably is also polished to inhibit integration. Coronally, anchoring screw body 12 incorporates an external polygonal, such as hexagonal, driving feature 12b for easy insertion and removal of the anchoring screw body. Intermediate to the external driving feature and external thread 12a is an outwardly, radially extending flange 12c that acts as a positive seating surface for the anchoring screw body at the time of insertion. Finally, the anchoring screw body incorporates an internal thread 12d which goes through the entire length of the body to resist the driving force of distraction jack screw 16, to be described, during the distraction procedure.

Distraction jack screw 16 shown in FIG. 1 has an externally threaded portion 16a adapted for threaded engagement with internal threads 12d of the anchoring screw body 12 and a distal cylindrical post portion 16b having a diameter selected so that the post portion can be received in bore 14a of base plug 14 bypassing threads 14b and bottom out at the closed end of the bore. Head 16c of distraction screw 16 has an outer diameter selected to fit within the bore of anchoring screw body 12 and is provided with a suitable internal polygonal driving feature 16d for driving the screw body toward base plug 14.

A first stage healing screw 18 shown in FIG. 2 has a threaded portion 18a selected to be threadingly received in internal threads 12d of anchoring screw body 12 and a distal cylindrical post portion 18b having a diameter selected to bypass threads 14b of base plug 14 and to be received in bore 14a. Head 18c has a diameter selected to generally match that of flange 12c and is provided with an annular recess 18d adapted to receive the driving feature 12b of anchoring screw body 12 with head 18c seated on flange 12c. Healing screw 18 is also provided with a suitable polygonal driving feature 18e to facilitate insertion and removal thereof.

After performing the osteotomy, base plug 14 is rigidly seated therein and anchoring screw body 12 is screwed into the bore leaving a selected gap g of about 1.0 mm between base plug 14 and anchoring screw body 12. A healing screw 18 is inserted, as seen in FIG. 3, and allowed to remain for a five day latency period before the distraction begins. During this latency period, the surrounding section of bone forms a callus, i.e., elastic cartilage tissue. During the healing process and before the callus calcifies, healing screw 18 is removed and distraction jack screw 16 is inserted and rotated a selected amount to drive end 16e of post portion 16b against plug 14 to commence the monofocal distraction of the healing callus. Indexing marks (not shown) are preferably provided on head 16c and anchor screw body 12 to provide a reference to determine the amount of rotation to be taken. Typically screw 16 is rotated sufficiently to provide approximately 1 mm of axial movement, that is, increasing gap g by 1 mm, each day until reaching the desired total length. A series of jack screws 16 can be provided having different selected lengths to accommodate various desired gaps. Once the desired gap is achieved the final jack screw 16 is inserted to depth and healing screw 19, FIG. 4, is inserted, as seen in FIGS. 4a and 4b, and allowed to remain for a suitable healing period, e.g., approximately a six week period to allow the callus to calcify. The healing screw 19 and the final jack screw 16 are then removed and the anchoring screw body 12 and base plug 14 are in turn removed. As a result of the procedure the bone has greatly proliferated to provide a suitable site for a conventional dental implant. Then the site is prepared for reception of a dental implant in a conventional manner using the existing osteotomy.

Thus it will be seen that the invention provides a maxillofacial anchoring and distracting system to effectively increase, by osteogenesis, the existing bone quantity. Once the desired bone mass is developed the unit can be removed from the osteotomy and replaced with an endosseous dental implant. Furthermore, the distraction system eliminates the need for harvesting tissue or using synthetic graft materials. Since endosseous dental implants can be used in succession with the disclosed distraction procedure, time, money and pain required to obtain functional masticatory results can be decreased.

Although the invention has been described with regard to a specific preferred embodiment thereof, variations and modifications will become apparent to those skilled in the art. It is, therefore, the intention that the appended claims be interpreted as broadly as possible in view of the prior art to include all such variations and modifications.

What is claimed:

1. A maxillofacial anchoring and distracting system comprising a generally cylindrical base plug having a longitudinal axis, a closed ended, threaded bore formed through a crestal end and extending along the longitudinal axis, an anchoring screw body having a longitudinal axis and having a longitudinally extending threaded bore extending through the anchoring screw body, the anchoring screw body having external threads, and an elongated generally cylindrical member having first and second ends, an externally threaded portion for threaded engagement in the threaded bore of the anchoring screw body and a post portion having a diameter selected to be received within the bore of the base plug bypassing the threaded bore of the screw body.

2. A maxillofacial anchoring and distracting system according to claim 1 in which the elongated member has a head portion at the first end having a diameter selected to fit within the threaded bore of the anchoring screw body, an internal polygonal driving feature being formed at the first end, the length of the elongated member being selected so that the external threads of the elongated member can be threadingly received in the threaded bore of the anchoring screw body with the post portion received in and bottoming out against the closed end of the bore of the base plug.

3. A maxillofacial anchoring and distracting system according to claim 1 in which the anchoring screw body has first and second ends, a polygonal external driving feature being formed at the first end and an outwardly, radially extending flange being formed between the driving feature and the external threads of the anchoring screw body to serve as a seating surface of the anchoring screw body in an osteotomy of a jaw.

4. A maxillofacial anchoring and distracting system according to claim 3 in which the elongated member has a head portion at the first end the head portion having a diameter which generally matches that of the flange of the anchoring screw body, the head portion being formed with an annular recess which receives the driving feature of the anchoring screw body when the elongated member is fully driven into the anchoring screw body.

5. A maxillofacial anchoring and distracting system according to claim 1 in which the base plug is formed with at least one longitudinally extending flat on its outer surface to permit passage of fluid from the closed end of the osteotomy when the base plug is inserted therein.

6. A maxillofacial anchoring and distracting system according to claim 1 in which the base plug has a smooth, polished outer surface.

7. A maxillofacial anchoring and distracting system according to claim 1 in which the anchoring screw body has a polished outer surface.

* * * * *